(12) United States Patent
Horne et al.

(10) Patent No.: US 6,824,991 B2
(45) Date of Patent: Nov. 30, 2004

(54) HUMAN BAD POLYPEPTIDES, ENCODING NUCLEIC ACIDS AND METHODS OF USE

(75) Inventors: William A. Horne, Cary, NC (US); Tilman Oltersdorf, Cardiff, CA (US)

(73) Assignee: IDUN Pharmaceuticals Inc., San Diego, CA (US)

( * ) Notice: Subject to any disclaimer, the term of this patent is extended or adjusted under 35 U.S.C. 154(b) by 620 days.

(21) Appl. No.: 09/922,378

(22) Filed: Aug. 3, 2001

(65) Prior Publication Data

US 2002/0037869 A1 Mar. 28, 2002

Related U.S. Application Data

(62) Division of application No. 09/376,154, filed on Aug. 17, 1999, now abandoned, which is a division of application No. 08/717,123, filed on Sep. 20, 1996, now Pat. No. 5,965,703.

(51) Int. Cl.$^7$ ............................................. G01N 33/68
(52) U.S. Cl. ....................................................... 435/7.1
(58) Field of Search .......................................... 435/7.1

(56) References Cited

U.S. PATENT DOCUMENTS

| | | | | |
|---|---|---|---|---|
| 4,683,195 A | 7/1987 | Mullis et al. | ................... | 435/6 |
| 4,683,202 A | 7/1987 | Mullis | ....................... | 435/91.2 |
| 4,754,065 A | 6/1988 | Levenson et al. | ........... | 562/564 |
| 4,800,159 A | 1/1989 | Mullis et al. | ............... | 435/91.2 |
| 5,352,771 A | 10/1994 | Kostic et al. | ............... | 530/345 |
| 5,663,316 A | 9/1997 | Xudong | ..................... | 536/23.5 |

FOREIGN PATENT DOCUMENTS

| WO | WO 96/13614 | 5/1996 |
|---|---|---|

OTHER PUBLICATIONS

Gyuris et al., "Cdil, a Human GI and S Phase Protein Phosphates That Associates with Cdk2," *Cell* 75: 791–803, 1993.

Ruden et al., "Generating Yeast Transcriptional Activators Containing No Yeast Protein Sequences," *Nature* 350: 250–252, 1991.

Sato et al., "Interactions Among Members of the Bcl–2 Protein Family Analyzed with a Yeast Two–Hybrid System," *Proc. Natl. Acad. Sci. USA* 91: 9238–9242, 1994.

Sinkovics et al., "Apoptosis by Genetic Engineering," *Leukemia* 8(1): S98–S102, 1994.

Ross et al., "Gene Therapy in the United States: A Five–Year Status Report," *Human Gene Therapy* 7: 1781–1790, 1996.

Wolff et al., "Direct Gene Transfer into Mouse Muscle in Vivo," *Science* 247: 1465–1468, 1990.

Yang et al., "Bad, a heterodimeric partner for Bcl–XL and Bcl–2, displaces Bax and promotes cell death," *Cell* 80: 285–291, Jan. 27, 1995.

*Primary Examiner*—Robert A. Wax
(74) *Attorney, Agent, or Firm*—Seed Intellectual Property Law Group PLLC

(57) ABSTRACT

The invention provides an isolated gene and an isolated nucleic acid sequence encoding human Bad and functional fragments thereof. Also provided is an isolated human Bad polypeptide and functional fragments thereof. Methods of identifying human Bad binding partners and methods of screening for compounds which interfere with the association of human Bad interacting polypeptides with human Bad are also provided. Finally, methods for decreasing or increasing the viability of a cell are provided as well.

8 Claims, 5 Drawing Sheets

```
GGGCCTAGGG CGCCGGGTCA GGGGCCTCGA GATCGGGCTT GGGCCCAGAG C ATG TTC           57
                                                         Met Phe
                                                           1

CAG ATC CCA GAG TTT GAG CCG AGT GAG CAG GAA GAC TCC AGC TCT GCA           105
Gln Ile Pro Glu Phe Glu Pro Ser Glu Gln Glu Asp Ser Ser Ser Ala
            5               10                  15

GAG AGG GGC CTG GGC CCC AGC CCC GCA GGG GAC GGG CCC TCA GGC TCC           153
Glu Arg Gly Leu Gly Pro Ser Pro Ala Gly Asp Gly Pro Ser Gly Ser
        20              25              30

GGC AAG CAT CAT CGC CAG GCC CCA GGC CTC CTG TGG GAC GCC AGT CAC           201
Gly Lys His His Arg Gln Ala Pro Gly Leu Leu Trp Asp Ala Ser His
    35              40              45              50

CAG CAG GAG CAG CCA ACC AGC AGC AGC CAT CAT GGA GGC GCT GGG GCT           249
Gln Gln Glu Gln Pro Thr Ser Ser Ser His His Gly Gly Ala Gly Ala
                55              60              65

GTG GAG ATC CGG AGT CGC CAC AGC TCC TAC CCC GCG GGG ACG GAG GAC           297
Val Glu Ile Arg Ser Arg His Ser Ser Tyr Pro Ala Gly Thr Glu Asp
            70              75              80

GAC GAA GGG ATG GGG GAG GAG CCC AGC CCC TTT CGG GGC CGC TCG CGC           345
Asp Glu Gly Met Gly Glu Glu Pro Ser Pro Phe Arg Gly Arg Ser Arg
        85              90              95

TCG GCG CCC CCC AAC CTC TGG GCA GCA CAG CGC TAT GGC CGC GAG CTC           393
Ser Ala Pro Pro Asn Leu Trp Ala Ala Gln Arg Tyr Gly Arg Glu Leu
    100             105             110

CGG AGG ATG AGT GAC GAG TTT GTG GAC TCC TTT AAG AAG GGA CTT CCT           441
Arg Arg Met Ser Asp Glu Phe Val Asp Ser Phe Lys Lys Gly Leu Pro
115             120             125             130

CGC CCG AAG AGC GCG GGC ACA GCA ACG CAG ATG CGG CAA AGC TCC AGC           489
Arg Pro Lys Ser Ala Gly Thr Ala Thr Gln Met Arg Gln Ser Ser Ser
            135             140             145

TGG ACG CGA GTC TTC CAG TCC TGG TGG GAT CGG AAC TTG GGC AGG GGA           537
Trp Thr Arg Val Phe Gln Ser Trp Trp Asp Arg Asn Leu Gly Arg Gly
            150             155             160
```

*Fig. 1A*

| | |
|---|---|
| AGC TCC GCC CCC TCC CAG TGACCTTCGG TCCACATCCC GAAATCCACC<br>Ser Ser Ala Pro Ser Gln<br>165 | 585 |
| CGTTCCCATT GCCCTGGGCA GCCATTTTGA ATATGGGAGG AAGTAAGTTC CCTCAGGCCT | 645 |
| ATGCAAAAAG AGGATCCGTG CTGTATCCTT TGGAGGGAGG GTTGACCCAG ATTCCCTTCC | 705 |
| GGTGTGTGTG AAGCCACGGA AGGTTGGTCC CATCGGAAGT TTTGGGTTTT CCGCCCACAG | 765 |
| CCGCCGGAAG TGGCTCCGTG GCCCCGCCCT CAGGTTCCGG GGTTTCCCCC AGGCGCCTGC | 825 |
| GCTAAGTAGC GAGCCAGGTT TAACCGTTGT GTCACCGGGA CCCGAGCCCC CGCGATGCCC | 885 |
| TGGGGGCCGT GATCAGTACC AAATGTTAAT AAAGCCCGCG TGTGTGCCAA AAAAAAAAA | 945 |
| A | 946 |

*Fig. 1B*

ALIGNMENT OF MOUSE AND HUMAN BAD PROTEIN SEQUEUNCES

```
             10         20         30         40
   1  M G T P K Q P S L A P A H A L G L R K S D P G I R S L G S D A G G R R W R P A A      PmBad
   1  - - - - - - - - - - - - - - - - - - - - - - - - - - - - - - - - - - - - - - - -      PBM1

50         60         70         80
  41  Q S M F Q I P E F E P S E Q E D A S A T D R G L G P S L T E D Q P G P Y - - - -      PmBad
   1  - - M F Q I P E F E P S E Q E D S S S A E R G L G P S P A G D G P S G S G K H H      PBM1

90        100        110        120
  77  - L A P G L L G S N I H Q Q G R A A T N S H H G G A G A M E T R S R H S S Y P A      PmBad
  39  R Q A P G L L W D A S H Q Q E Q P T S S S H H G G A G A V E I R S R H S S Y P A      PBM1

130        140        150        160
 116  G T E E D E G M E E E L S P F R G R S R S A P P N L W A A Q R Y G R E L R R M T      PmBad
  79  G T E D D E G M G E E P S P F R G R S R S A P P N L W A A Q R Y G R E L R R M S      PBM1

170        180        190        200
 156  D E F E G S F K - G L P R P K S A G T A T Q M R Q S A G W T R I I Q S W W D R N      PmBad
 119  D E F V D S F K K G L P R P K S A G T A T Q M R Q S S S W T R V F Q S W W D R N      PBM1

210
 195  L G K G G S T P S Q                                                                   PmBad
 159  L G R G S S A P S Q                                                                   PBM1
```

PmBad = mouse protein sequence
PBM1 = human protein sequence

*Fig. 2*

HUMAN BAD POLYPEPTIDES, ENCODING NUCLEIC ACIDS AND METHODS OF USE

CROSS-REFERENCE TO RELATED APPLICATIONS

This application is a divisional of U.S. application Ser. No. 09/376,154 now abandoned, filed Aug. 17, 1999, which application is a divisional of U.S. application Ser. No. 08/717,123, filed Sep. 20, 1996, which issued as U.S. Pat. No. 5,965,703 on Oct. 12, 1999.

Throughout this application various publications are referenced within parentheses. The disclosures of these publications in their entireties are hereby incorporated by reference in this application in order to more fully describe the state of the art to which this invention pertains.

BACKGROUND OF THE INVENTION

The present invention relates generally to apoptosis or, programed cell death, and more particularly, nucleic acids encoding human Bad polypeptides which can be used to modulate apoptosis for the therapeutic treatment of human diseases.

Apoptosis is a normal physiological process of cell death that plays a critical role in the regulation of tissue homeostasis by ensuring that the rate of new cell accumulation produced by cell division is offset by a commensurate rate of cell loss due to death. It has now become clear that disturbances in apoptosis, also referred to as physiological cell death or programmed cell death, that prevent or delay normal cell turnover can be just as important to the pathogenesis of diseases as are known abnormalities in the regulation of proliferation and the cell cycle. Like cell division, apoptosis is similarly regulated under normal circumstances through complex interaction of gene products that either promote or inhibit cell death.

The stimuli which regulate the function of these apoptotic gene products include both extracellular and intracellular signals. Either the presence or the absence of a particular stimuli can be sufficient to evoke a positive or negative apoptotic signal. For example, physiological stimuli that prevent or inhibit apoptosis include, for example, growth factors, extracellular matrix, CD40 ligand, viral gene products neutral amino acids, zinc, estrogen and androgens. In contrast, stimuli which promote apoptosis include growth factors such as tumor necrosis factor (TNF), Fas, and transforming growth factor $\beta$ (TGF$\beta$) neurotransmitters, growth factor withdrawal, loss of extracellular matrix attachment, intracellular calcium and glucocorticoids, for example. Other stimuli, including those of environmental and pathogenetic origins, also exist which can either induce or inhibit programmed cell death.

Thus, apoptosis is mediated by diverse signals and complex interactions of cellular gene products which ultimately result in a cell death pathway that is required to regulate normal tissue homeostasis.

Several gene products which modulate the apoptotic process have now been identified. Although these products can in general be separated into two basic categories, gene products from each category can function to either inhibit or induce programmed cell death. One family of gene products are those which are members of the Bcl-2 family of proteins. Bcl-2, is the best characterized member of this family and inhibits apoptosis when overexpressed in cells. Other members of this gene family include, for example, Bax, Bak, $BCl-x_L$, $Bcl-x_S$, and Bad. While some of these proteins can prevent apoptosis, others such as Bax, $Bcl-x_S$ and Bak function to augment apoptosis.

A second family of gene products which modulate the apoptotic process is the family of proteases known as aspartate-specific cysteine proteases (ASCPs). These proteases are related genetically to the ced-3 gene product which was initially shown to be required for programmed cell death in the roundworm, C. elegans. The ASCPs family of proteases includes, for example, human ICE (interleukin-1-$\beta$ converting enzyme), $ICH-1_S$, $ICH-1_S$, CPP32, Mch2, Mch3, ICH-2 and $ICE_{rel}$-III. One common feature of these gene products is that they are cysteine proteases with specificity for substrate cleavage at Asp-X bonds. Although these proteases induce cell death when expressed in cells, several alternative structural forms such as ICE$\delta$, ICE$\epsilon$, $ICH-1_S$ and Mch2$\beta$ are known which actually function to inhibit apoptosis.

In addition to the Bcl-2 and ASCP gene families which play a role in apoptosis in mammalian cells, it has become increasingly apparent that other gene products exist which are important in mammalian cell death and which have yet to be identified. For example, in addition to Ced-3, another C. elegans gene known as Ced-4 exists which is also required for programmed cell death in C. elegans. However, mammalian homologues of this protein remain elusive and have not yet been identified Further, it is ambiguous as to whether other genes exist which belong to either of the above two apoptotic gene families or what role they may play in the programmed cell death pathway. Finally, it is also unclear what the physiological control mechanisms are which regulate programmed cell death or how the cell death pathways interact with other physiological processes within the organism.

The maintenance of tissue homeostasis is required in a range of physiological processes such as embryonic development and immune cell regulation as well as in normal cellular turnover. The dysfunction, or loss of regulated apoptosis can lead to a variety of pathological disease states. For example, the loss of apoptosis can lead to the pathological accumulation of self-reactive lymphocytes such as that occurring with many autoimmune diseases. Inappropriate loss of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury.

Treatments which are specifically designed to modulate the apoptotic pathways in these and other pathological conditions can change the natural progression of many of these diseases. However, since distinct differences are known to exist between human and other species such as C. elegans, it is advantageous to use human proteins for the production of biopharmaceuticals as well as other molecules or compounds which are produced to modify the function of a regulator of programed cell death. The use of human proteins as both biopharmaceuticals and to identify compounds is also important in regard to the therapeutic efficacy and safety of the treatment. For example, the half-life of non-human proteins can be comprised in a heterologous environment and the induction of a host immune response against a non-human protein can be potentially dangerous to the patient.

Thus, there exists a need to identify new apoptotic genes and their human homologues and for methods of modulating apoptotic process for the therapeutic treatment of human diseases. The present invention satisfies this need and provides related advantages as well.

SUMMARY OF THE INVENTION

The invention provides an isolated gene and an isolated nucleic acid sequence encoding human Bad and functional fragments thereof. Also provided is an isolated human Bad polypeptide and functional fragments thereof. Methods of identifying human Bad binding partners and methods of screening for compounds which interfere with the association of human Bad interacting polypeptides with human Bad are also provided. Finally, methods for decreasing or increasing the viability of a cell are provided as well.

BRIEF DESCRIPTION OF THE DRAWINGS

FIG. 1 shows the nucleotide and predicted amino acid sequence of human Bad (SEQ ID NOS:1 and 2, respectively).

FIG. 2 shows a comparison of the amino acid sequence between human Bad (SEQ ID NO: 2; clone PBM1) and mouse Bad (SEQ ID NO: 3; PmBad). The boxed regions emphasize amino acid identities and differences.

DETAILED DESCRIPTION OF THE INVENTION

Figure 3:
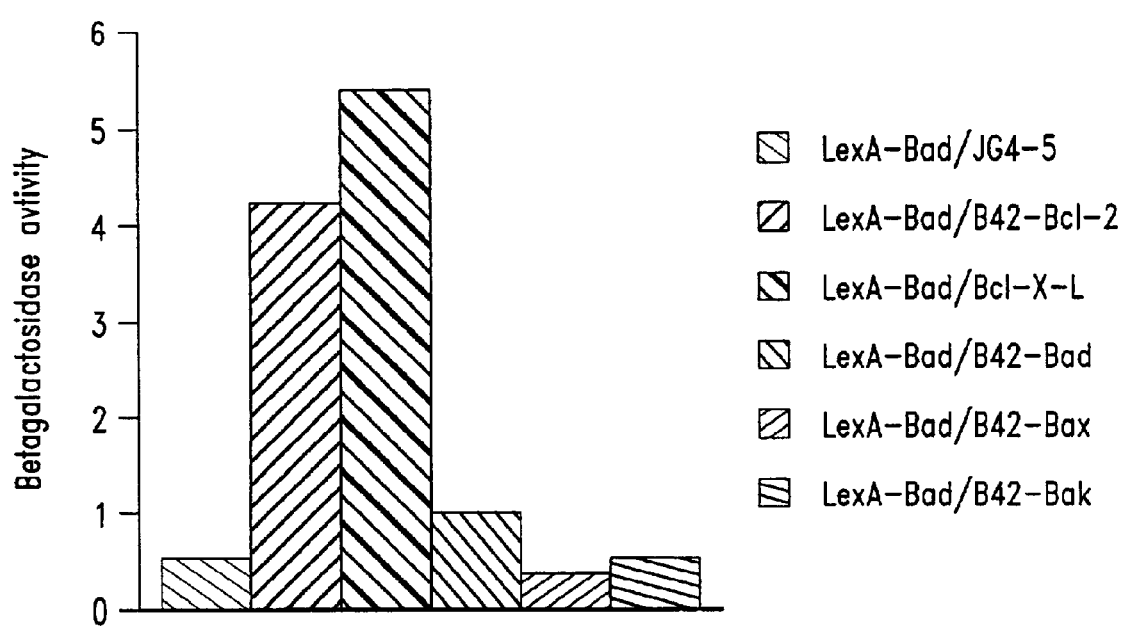
FIG. 3 shows binding interactions between human Bad and Bcl-2 and between human Bad and Bcl-$X_L$ in a yeast two-hybrid assay.

This invention is directed to the human Bcl-$x_L$/Bcl-2 associated death (Bad) promoting polypeptide and encoding nucleic acids. This protein is a member of the Bcl-2 family of cell death regulatory proteins in that it shows sequence homology with this family of proteins and is able to bind Bcl-$x_L$ and to Bcl-2. The binding of human Bad to Bcl-$x_L$ results in the induction of programmed cell death. The binding properties of human Bad to Bcl-$x_L$ have been found to be different from the properties of Bax and Bak, two other death-enhancing Bcl-2 family proteins.

For example, amino-terminal deletions in Bax which create a fragment leaving the BH-1 and BH-2 domains intact completely abolish the ability of this fragment to interact with Bcl-$X_L$. In contrast, equivalent truncations of Bad leave the ability of this fragment to bind Bcl-$x_L$ intact. This difference in interaction can have therapeutic advantages because compounds can be used which selectively target interactions of Bad and suppress programed cell death without interfering with other cell death regulatory proteins.

In one embodiment, the invention is directed to nucleic acids encoding human Bad. The nucleic acids are used to produce recombicant Bad polypeptides which can be used in screening assays to identify compounds that interfere with Bad function. These screening assays yield compounds that antagonize the function of Bad and thus will prevent apoptosis. Such pharmaceutical compounds are useful for the treatment or prevention of diseases which are characterized by apoptotic cell death. Alternatively, assays can be configured to yield compounds that exhibit substantially the same function as, or "mimic" the function of Bad and thus enhance apoptosis. These pharmaceutical compounds are useful for the treatment or prevention of diseases which are characterized by the loss of apoptotic cell death. Human Bad polypeptides can also be used to identify novel interacting polypeptides and to identify the binding domains within these proteins as well as within known binding polypeptides such as Bcl-$X_L$. Similarly, these novel binding polypeptides and binding domains can be used to inhibit or enhance apoptosis or to identify compounds which modulate their apoptotic function.

As used herein, the term "substantially" when referring to the human Bad nucleotide or amino acid sequence is intended to refer to the degree to which two sequences of between about 15–30 or more nucleotides in length, are identical or similar so as to be considered by those skilled in the art to be functionally equivalent. For example, the human Bad nucleic acid of the invention has a nucleotide sequence substantially the same as that shown in FIG. 1 and as SEQ ID NO:1. Thus, if a second sequence is substantially the same as that shown as SEQ ID NO:1 so as to selectively hybridize, then it is considered functionally equivalent by those skilled in the art. Methods for sequence comparisons and determinations of similarity are well known and routine within the art.

Functionally equivalent nucleic acid sequences include, for example, sequences that are related, but different and encode the same human Bad polypeptide due to the degeneracy of the genetic code as well as sequences that are related, but different and encode a different human Bad polypeptide that exhibits similar functional activity. In both cases, the nucleic acids encode functionally equivalent gene products. Functional fragments of human Bad encoding nucleic acids such as oligonucleotides, polyoligonucleotides, primers and modified forms thereof are also considered to be within the definition of the term and the invention as claimed. Modified forms of functionally equivalent nucleic acid sequences include, for example, chemical modifications or derivatives such as those used in antisense therapy. Functional equivalency is also relevant to human Bad nucleic acids which do not encode gene products, for example, but instead are functional elements in and of themselves. Specific examples of such functional nucleic acids include, for example, promoters, enhances and other gene expression regulatory elements.

Human Bad polypeptides of the invention have an amino acid sequence substantially similar to that shown in FIG. 1 and in SEQ ID NO:2. Functionally equivalent human Bad amino acid sequences similarly includes, for example, related, but different sequences so long as the different polypeptide exhibits at least one functional activity of human Bad. Specific examples of Bad polypeptide functional activities include functions such as the ability to bind or otherwise interact with Bad interacting polypeptides and/or Bad binding partners and the ability to promote cell death by heterdimerization with, for example, Bcl-$x_L$ and Bcl-2. Related, but different polypeptides also include, for example, substitutions of conserved and/or non-essential amino acids within the Bad polypeptide sequence. Fragments and functional domains of human Bad are similarly included within the definition of the term and the claimed invention.

Therefore, it is understood that limited modifications may be made without destroying the biological function of the human Bad polypeptide and that only a portion of the entire primary structure may be required in order to effect activity. For example, minor modifications of the human Bad amino acid sequence (SEQ ID NO:2) which does not destroy its activity also fall within the definition of human Bad and within the definition of the polypeptide claimed as such. Also, for example, genetically engineered fragments of human Bad either alone or fused to heterologous proteins such as fusion proteins that retain measurable enzymatic or other biological activity fall within the definition of the polypeptides as claimed.

It is understood that minor modifications of primary amino acid sequence may result in polypeptides which have substantially equivalent or enhanced function as compared to the sequences set forth in FIG. 1 (SEQ ID NO:2). These modifications may be deliberate, as through site-directed mutagenesis, or may be accidental such as through mutation in hosts which are human Bad producers. All of these modifications are included as long as human Bad biological function is retained. Further, various molecules can be attached to human Bad, including for example, other proteins, carbohydrates, lipids, or chemical moieties. Such modifications are included within the definition of human Bad polypeptides.

As used herein, the term "Bad interacting polypeptide" is intended to mean a peptide, polypeptide or protein which interacts directly or indirectly with the human Bad polypeptide. Such polypeptides include, for example, Bcl-$x_L$ and Bcl-2. When associated with human Bad, these interacting polypeptides form a heterodimer with the human Bad polypeptide. Direct interaction can include the direct binding of human Bad polypeptide with the interacting polypeptide. Binding can occur, for example, through polypeptide-polypeptide binding interaction or through binding involving post-translational modifications. Examples of post-translational modifications can include phosphorylation, glycosylation, acylation and lipidation. Indirect interaction between Bad and Bad interacting polypeptides can include, for example, the interaction of human Bad with a docking protein such as an SH2 or SH3 containing protein with functions to regulate the activity of a cell death protein proximal in the human Bad pathway. Human Bad interacting polypeptides can enhance Bad activity such as by augmenting the interaction of Bad with Bcl-$x_L$ or Bcl-2 or with other cell death regulatory molecules. Alternative, human Bad interacting polypeptides can inhibit Bad activity by preventing the interaction of Bad with, for example, Bcl-$x_L$, Bcl-2 or other cell death regulatory molecules. Similarly, such interactions can occur directly or indirectly.

As used herein, the term "human Bad binding partner" is intended to mean polypeptides, non-polypeptide mimetics, organic molecules and other compounds which bind to the human Bad polypeptide. As with human Bad interacting polypeptide, human Bad binding partners can either inhibit or enhance the function of Bad through the binding of these partners to human Bad.

The invention provides a gene encoding human Bad or functional fragment thereof. The invention also provides an isolated nucleic acid sequence encoding human Bad or fragment thereof. The gene and nucleic acid sequences encode substantially the sequence as shown in SEQ ID NO:1. Fragments of the gene or nucleic acid sequence are provided which comprise single or double stranded nucleic acids having substantially the sequences shown in SEQ ID NO:1.

The human Bad nucleic acids of the present invention were identified by searching a human database of expressed sequence tags (ESTs) to identify potential new sequence fragments which may have homology to the mouse Bad gene and other Bcl-2 family cell death regulators. This approach was chosen because the standard approach of using the mouse sequence to probe human cDNA libraries had failed in this case as described in the Examples. Searches of the EST database identified short ESTs containing partial nucleotide sequence homology to the mouse Bad nucleotide sequence. These EST sequences were then used to design probes for the screening of cDNA libraries. Screening with the EST derived probes resulted in the identification of a putative human Bad nucleotide sequence which encoded a protein with approximately 77% amino acid homology to mouse Bad with the exception of an apparent truncation of 42 amino acids at the amino terminus. A comparison of the amino acid sequence between human Bad (SEQ ID NO: 2) and mouse Bad (SEQ ID NO: 3) is shown in FIG. 2. Unexpectedly, this apparent truncation has now been shown to be the authentic amino terminus of human Bad.

In regard to the search for potential new sequences having homology to mouse Bad and other Bcl-2 family members, there are numerous considerations which must be taken into account when searching for homologies from unknown sequences such as ESTs fragments. For example, searching a genetic data base will yield homologous sequence matches to essentially any query nucleotide sequence. However, in order for the search to result in a meaningful match, additional criteria and permutations must be used to identify the authentic homologue of interest from among the non-specific homology matches. Mouse Bad shares the highest degree of homology with other Bcl-2 related proteins in the region believed to contain the binding site with Bcl-$X_L$ and Bcl-2. A given EST returned by the search may not include one of these functionally important highly homologous sites, but rather, may only include a region within the polypeptide with cryptic homology. Confirming an EST as an actual Bad or BH1 and BH2 encoding polypeptide involves translation of all positive EST hits in three different reading frames and subsequent identification of conservative sequence homologies to the gene of interest. Then, using conventional cDNA cloning, a full length cDNA of the putative novel gene can be obtained and 1) analyzed for overall structural homology to Bad and Bcl-2 family members, 2) recombinantly expressed and analyzed for binding activity to other Bcl-2 family proteins and 3) analyzed for the induction or suppression of programmed cell death by heterologous expression of the cDNA in appropriate cells.

Alternative methods than that described above for isolating human Bad encoding nucleic acids can similarly be employed. For example, using the teachings described herein, those skilled in the art can routinely isolate and manipulate human Bad nucleic acids using methods well known in the art. All that is necessary is the sequence of the human Bad encoding nucleic acids (FIG. 1 and SEQ ID NO:1) or its amino acid sequence (FIG. 1 and SEQ ID NO:2) Such methods include, for example, screening a cDNA or genomic library by using synthetic oligonucleotides, nucleic acid fragments or primers as hybridization probes. Alternatively, antibodies to the human Bad amino acid sequence or fragments thereof can be generated and used to screen an expression library to isolate human Bad encoding nucleic acids. Other binding reagents to human Bad polypeptides, such as Bcl-$X_L$ or fragments thereof can similarly be used to isolate human Bad polypeptides having substantially the amino acid sequence show in FIG. 1.

In addition, recombinant DNA methods currently used by those skilled in the art include the polymerase chain reaction (PCR) which, combined with the human Bad nucleotide and amino acid sequences described herein, allows reproduction of human Bad encoding sequences. Desired sequences can be amplified exponentially starting from as little as a single gene copy by means of PCR.

The PCR technology is the subject matter of U.S. Pat. Nos. 4,683,195, 4,800,159, 4,754,065, and 4,683,202 all of which are incorporated by reference herein.

The above described methods are known to those skilled in the art and are described, for example, in Sambrook et al., *Molecular Cloning: A Laboratory Manual*, Cold Spring Harbor Laboratory, New York (1992) and the various references cited therein and in Ansubel et al., *Current Protocols in Molecular Biology*, John Wiley and Sons, Baltimore, Md. (1989); and in Harlow et al., *Antibodies: A Laboratory Manual*, Cold Spring Harbor Laboratory, New York (1989). These references and the publications cited therein are hereby expressly incorporated herein by reference.

The invention provides an isolated human Bad polypeptide comprising substantially the amino acid sequence as that shown in FIG. 1 (SEQ ID NO:2). Human Bad functional fragments are also provided. A specific example of a human Bad functional fragment is the Bcl-$X_L$ binding domain.

Isolated human Bad polypeptides of the invention can be obtained by a variety of methods known within the art. For example, the isolated peptides can be purified by biochemical methods including, for example, affinity chromatography. Affinity matrices which can be used for human Bad isolation can be anti-human Bad monoclonal or polyclonal antibodies prepared against the amino acid sequence shown in FIG. 1 (SEQ ID NO:2), or fragments thereof such as synthetic peptides, recombinant fragments or the like. Alternatively, cognate binding domains or polypeptides as well as other compounds known in the art which specifically bind to human Bad can similarly be used as affinity matrices to isolate substantially pure human Bad polypeptides of the invention.

Human Bad polypeptides can also be produced by recombinant methods known to those skilled in the art. Recombinant human Bad polypeptides include, for example, an amino acid sequence substantially the same as that shown in FIG. 1 (SEQ ID NO:2) as well as fusion proteins and fragments thereof. The human Bad encoding nucleic acids can be cloned into the appropriate vectors for propagation, manipulation and expression. Such vectors are known or can be constructed by those skilled in the art and should contain all expression elements necessary for the transcription, translation, regulation, and if desired, sorting of the human Bad polypeptides. The vectors can also be for use in either prokaryotic or eukaryotic host systems so long as the expression and regulatory elements are of compatible origin. One of ordinary skill in the art will know which host systems are compatible with a particular vector. The recombinant polypeptides produced can be isolated by, for example, the methods described above.

Apoptosis plays a significant role in numerous pathological conditions in that programmed cell death is either inhibited, resulting in increased cell survival, or enhanced which results in the loss of cell viability. Examples of pathological conditions in which increased cell survival contributes to the disease process include cancers in general, and more particularly cancers such as lymphomas and hormone dependent tumors. Such hormone dependent tumors include, for example, breast, prostate and ovarian cancer. Inhibition of programed cell death of immune cells plays a role in autoimmune diseases such as systemic lupus erythematosus and immune-mediated glomerulonephritis. Viruses such as herpesvirus, poxvirus and adenovirus carry anti-apoptotic genes to prolong production or viral particles by the host cell by preventing the host cell from committing suicide.

In contrast, apoptotic diseases where enhanced programed cell death is part of the disease process generally include, for example, neurodegenerative disorders such as Alzheimer's disease, Parkinson's disease, Amyotrophic lateral sclerosis, Retinitis pigmentosa, and Cerebellar degeneration. Other diseases associated with increased apoptosis include, for example, myelodysplastic syndromes such as aplastic anemia and ischemic injury including myocardial infarction, stroke and reperfusion injury.

The human Bad encoding nucleic acids and polypeptides of the invention can be used to diagnose, treat or reduce the severity of cell death mediated diseases such as those described above as well as other diseases mediated by either increased or decreased programmed cell death. Additionally, the human Bad encoding nucleic acids and polypeptides of the invention can be used to screen for pharmaceutical compounds and macromolecules which inhibit or promote human Bad mediated programmed cell death.

For example, the human Bad encoding nucleic acids, polypeptides and functional fragments thereof can be used to diagnose, or to generate reagents to diagnose diseases mediated or characterized by programed cell death. Diagnosis can be by, for example, nucleic acid probe hybridization with human Bad containing nucleotide sequences or by antibody or ligand mediated detection with human Bad binding agents. Such methods are routine to those skilled in the art. Detection can be performed ex vivo, for example, by removing a cell or tissue sample from an individual exhibiting or suspected of exhibiting a cell death mediated disease. Correlation of increased human Bad expression or activity is indicative of diseases characterized by enhanced programmed cell death whereas correlation of decreased human Bad expression or activity is indicative of diseases characterized by the suppression of programmed cell death.

The above human Bad polypeptides can also be formulated into pharmaceutical compositions known within the art for the treatment of cell death mediated diseases characterized by increased cell survival and proliferation. Functional fragments, including peptides and peptide mimetics corresponding to the Bcl-$X_L$ binding domain of human Bad can similarly be formulated for the treatment of such diseases associated with increased cell survival and proliferation. Administration of human Bad polypeptides and functional fragments thereof will induce apoptosis in treated cells and eliminate those cells characterized by increased cell survival or proliferation. Administration of non-human Bad polypeptides, molecules or compounds that induce the activation, regulation or expression of human Bad can similarly be used for the treatment of diseases characterized by increased cell survival and proliferation. Specific examples of such polypeptides, molecules and compounds include Bad interacting polypeptides, binding partners and non-peptide compound equivalents.

To be effective, the human Bad polypeptides must be introduced into the cells characterized by increased cell survival. Introduction can be accomplished by a variety of means known within the art including, for example, lipid vesicles and receptor mediated endocytosis. Targeting to the appropriate cell type can similarly be accomplished through conjugation to specific receptor ligands, specific target cell antibodies and the like.

The human Bad polypeptides are administered by conventional methods, in dosages which are sufficient to induce apoptosis in the cells characterized by increased cell survival or proliferation. Such dosages are known or can be easily determined by those skilled in the art. Administration can be accomplished by, for example, intravenous, intraperitoneal or subcutaneous injection. Administration can be performed in a variety of different regimens which include single high dose administration or repeated small dose administration or a combination of both. The dosing will depend on the cell type, progression of the disease and overall health of the individual and will be known or can be determined by those skilled in the art.

In contrast to the induction of human Bad mediated apoptosis for the treatment of pathological conditions characterized by increased cell survival or proliferation, inhibitors of human Bad can be used to treat diseases characterized by increased programmed cell death. Such inhibitors can be, for example, binding domain inhibitors, including small non-peptide, organic molecule inhibitors. Such inhibitors are formulated in a medium which allows introduction into the desired cell type. Alternatively, such inhibitors can be attached to targeting ligands for introduction by cell mediated endocytosis and other receptor mediated events.

Other inhibitors of human Bad include, for example, small molecules and organic compounds which bind and inactivate human Bad by a competitive or non-competitive type mechanism. Molecules, polypeptides or compounds which indirectly inhibit the human Bad pathway can also be used as inhibitors of human Bad. Indirect inhibition can be accomplished by, for example, inhibition of Bad interacting polypeptides with Bad. Such inhibition includes, for example, the inhibition of binding events as well as post-translational modifications which function in promoting human Bad mediated cell death. Human Bad inhibitors can be identified by screening for molecules which demonstrate specific or beneficial human Bad inhibitory activity. Such methods are described further below and can be practiced by those skilled in the art given the human Bad nucleotide and amino acid sequences described herein.

Treatment or reduction of the severity of cell death mediated diseases can also be accomplished by, for example, introducing expressible nucleic acids encoding human Bad polypeptides or functional fragments thereof into cells characterized by such diseases. For example, elevated synthesis rates of human Bad can be achieved by, for example, using recombinant expression vectors and gene transfer technology. Similarly, treatment or reduction of the severity of cell death mediated diseases can also be accomplished by introducing and expressing antisense human Bad nucleic acids so as to inhibit the synthesis rates of human Bad. Such methods are well known within the art and include, for example, the introduction of a compatible expression vector into population of cells characterized by either increased or decreased programmed cell death. Vectors can include, for example, both DNA and RNA viral vectors. Adenovirus is a specific example of a DNA viral vector.

Other methods of antisense inhibition known in the art include, for example, the use of synthetic oligonucleotides which are permeable to the cell membrane. Such oligonucleotides can include methylphosphonate and thiophosphonate chemical moieties for facilitating membrane permeability. The oligonucleotide can be employed for antisense inhibition of RNA processing, transport or translation events, or alternatively, oligonucleotides which form triple helices can be used for the inhibition of transcription. Such methods are well known in the art.

The vector to be used in the methods of the invention will depend on desired cell type to be targeted. For example, if neurodegenerative diseases are to be treated by decreasing the human Bad activity of affected neuronal cells then a vector specific for cells of the neuronal cell lineage should be used. Likewise, if diseases or pathological conditions of the hematopoietic system are to be treated, than a viral vector that is specific for blood cells and their precursors, preferably for the specific type of hematopoietic cell, should be used. Moreover, such vectors can additionally be modified with specific receptors or ligands and the like to modify or alter target specificity through receptor mediated events. These modification procedures can be performed by, for example, recombinant DNA techniques or synthetic chemistry procedures. The specific type of vector will depend upon the intended application. The actual vectors are also known and readily available within the art or can be constructed by one skilled in the art using methodology well known to those skilled in the art.

Vectors containing human Bad nucleic acids or inhibitors of human Bad such as antisense nucleic acids can be administered in several ways to obtain expression and therefore either increase or decrease the activity of human Bad in the cells affected by the disease or pathological condition. If viral vectors are used, for example, the procedure can take advantage of their target specificity and consequently, do not have to be administered locally at the diseased site. However, local administration can provide a quicker and more effective treatment. Administration can also be performed by, for example, intravenous or subcutaneous injection into the subject. Injection of the viral vectors into the spinal fluid can also be used as a mode of administration, especially in the case of neurodegenerative diseases.

Transfection vehicles such as liposomes can be used to introduce the non-viral vectors into recipient cells within and inoculated area. Such transfection vehicles are known by one skilled within the art. Alternatively, non-targeting vectors can be administered directly into a tissue of any individual. Such methods are known within the art and are described by, for example, Wolff et al. (*Science* 247:1465–1468 (1990)).

Additional features can be added to the vectors to ensure safety and/or enhance therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce mutant forms of human Bad, dysfunction of apoptosis will not occur.

As described previously, the human Bad encoding nucleic acids and human Bad polypeptides of the invention can be used to screen for compounds which inhibit or enhance the activity of human Bad. Such compounds can act directly or indirectly on human Bad, human Bad binding partners or human Bad interacting polypeptides. Such screening methods are known to those skilled in the art and can be performed by either in vitro or in vivo procedures. For example, described in Example II is a specific in vivo assay for human Bad binding activity. Also described therein is the identification of a human Bad binding domain which can be used as an inhibitory compound for human Bad binding activity. Moreover, this binding domain can also be used to model alternative inhibitors of human Bad and human Bad binding partners. Methods other than that described in Example II can also be used to screen and identify compounds which inhibit human Bad. Specific examples include the in vitro screening of small molecule libraries such as those produced by combinatorial chemistry. Phage display peptide libraries can similarly be screened for inhibitory polypeptides. Such libraries offer the advantages of producing greater than $10^8$ peptide sequences which can be screened in a single round of panning. These methods as well as others are known within the art and can be utilized to identify compounds which inhibit or enhance human Bad binding activity.

It is understood that modifications which do not substantially affect the activity of the various embodiments of this invention are also included within the definition of the invention provided herein. Accordingly, the following examples are intended to illustrate but not limit the present invention.

EXAMPLE I

Cloning and Characterization of Human Bad

This Example shows the cloning and sequence analysis of human Bad. The results described herein indicate that human Bad is a unique member of the BH1 and BH2 containing cell death regulatory polypeptides.

For the isolation of the human bad cDNA, an EST database was searched using the mouse protein sequence as a search criteria. However, prior to the use of the below described approach using expressed sequence tags (EST), two human c-DNA libraries were initially screened with a mouse bad probe under low stringency conditions. No human bad clones were identified using this approach. An EST derived probe subsequently led to the isolation of human bad c-DNA clones from the same libraries.

Subsequent to the above conventional approach, the EST database (NCBI) was searched with a 204 amino acid mouse protein sequence using the BLAST network service. Initial search attempts resulted in partial sequences showing limited homology to the search query. Briefly, an EST sequence was identified that had 25 out of 32 identical amino acids in the region corresponding to mouse residues 100–131 and 7 out of 7 identical amino acids in a region corresponding to mouse residues 147–153. Overall, this EST sequence was 364 nucleotides in length and exhibited an overall sequence homology to the mouse sequence of 72% at the nucleotide level. Differences in nucleotide sequence between the actual EST and the corresponding mouse sequence were apparent and likely resulted from no less than 37 sequencing errors (additions, deletions and ambiguities) causing amino acid frame shifts. As a result, only 32 out of a potential 109 amino acids (29%) actually aligned with the query sequence. Nevertheless, this partial EST sequence homology tentatively identifies a partial cDNA encoding human Bad (EST #171560, GenBank #H18135) and was used to screen human cDNA libraries so as to identify, characterize and confirm the existence of the human Bad cDNA and polypeptide.

Human cDNA libraries were screened using a 200 bp fragment amplified from the above putative human Bad EST. The 200 bp fragment was labeled with $^{32}$P-dCTP and then used to screen libraries derived from human substantia nigra, bone marrow and placenta. Screening methods were used were those known in the art and which are essentially described in Sambrook et al., *Molecular Cloning: A Laboratory Manual*, Cold Spring Harbor Laboratory, New York (1992). Briefly, $10^6$ plaque forming units were screened per library using a commercially available hybridization buffer, Quick Hybe (Stratagene) containing the above described putative human Bad EST probe. To identify positive plaques, duplicate filters were washed three times in 1× SSC and exposed to X-OMAT film (Kodak).

Screening of the each library resulted in the identification of putative cDNAs encoding human Bad. Surprisingly, none of these cDNAs appeared to be full length when compared to the corresponding mouse Bad sequence. For example, two partial cDNA's were isolated from substantia nigra and encoded 95 amino acids of the 3' end of Bad. Similarly, seven partial cDNAs were isolated from a placental cDNA library and three from a bone marrow library. Again, these cDNAs were truncated in that they encoded sequences substantially shorter than the mouse Bad sequence. A sequence comparison of each of these cDNAs revealed that all shared identical nucleotide sequence in the region identified as the open reading frame. However, when compared to the mouse Bad nucleotide and predicted amino acid sequence all of these isolated clones appeared to be truncated at their 5' ends.

Further sequence analysis of each of these clones revealed that the longest clone, termed BM1, exhibited a truncation of approximately 42 amino acids compared to the initiation methionine of the mouse sequence. Nevertheless, these apparently partial human Bad cDNA clones exhibited a predicted open reading frame that initiated with an amino terminal methionine. A further comparison of the nucleotide and encoding amino sequence revealed a 84% nucleotide identity and a 77% amino acid identity when compared to the mouse sequence. Thus, the similarity in sequence identity together with the apparent amino terminal truncation lead to the initial conclusion that the longest of the human Bad cDNA clones was probably less than full length. Surprisingly however, after further attempts to isolate a longer clone and after numerous experimentations that independently assessed the apparent authenticity of the methionine as a translation initiator present in human clones, it was concluded that the BM1 clone (SEQ ID NO: 1) and shown in FIG. 1 as human Bad was the full length human sequence. The predicted amino acid sequence of human Bad is also shown in FIG. 1 and as SEQ ID NO:2. FIG. 2 shows the amino acid alignments of human and mouse Bad. The experimentation yielding these conclusions are described further below.

To verify that cDNA BM1 encodes full length human Bad, the 5' sequence of a number of different cDNAs were analyzed. The results of that analysis revealed that seven different human placenta clones and three different human bone marrow clones terminated less that 54 nucleotides upstream from the above described proposed start methionine. In addition, two subsequently entered EST sequences of 317 and 300 nucleotides in length and having some similarlity to the above described human Bad cDNA were also found to terminate in this region. In all cases, the sequence around the start methionine satisfied Kozac criteria (A at-3 position). Also isolated were two clones from placenta (PL14 and PL21) which differed from other isolates in sequence just 5' to above described start methionine. In contrast, the sequence in this 5' region contains a consensus site for an RNA splicing junction and is similar to the mouse Bad sequence. Taken together, the above results indicate that there can be alternatively spliced forms of human Bad.

EXAMPLE II

Human Bad Binding Partners

This Example shows that Human Bad can bind to BCl-$X_L$.

To assess whether Bcl-2 family members bind to or otherwise interact with human Bad and to map their binding domains, a yeast two-hybrid system was employed using the above described clones. Briefly, the full length human Bad sequence was subcloned into the yeast 2-hybrid vector pEGE202, or "bait-vector" to express Bad as a fusion protein with the DNA-binding protein LexA (Ruden et al., Nature (1991) 350:426–430). Human Bcl-2, Bcl-X, Bax, Bak and Bad were similarly cloned into the yeast 2-hybrid vector pJG4-5, or "prey-vector" to expressed these Bcl-2 family members as fusion proteins with the transcriptional activator B42 (Gyuris et al., Cell (1993) 75:791–803). Briefly, the full length human Bad sequence was amplified by PCR and subcloned into the bait-vector. For the PCR reaction we used the following primers: 5'ATC AGT GAA TTC ACT ATG TTC CAG ATC CCA GAC3' (SEQ ID NO: 4) and 5'ATC GAT CTC GAG TCA CTG GGA GGG GGC GGA GCT3' (SEQ ID NO: 5). The resultant PCR fragment was digested with EcoRI and Xho I and then subcloned into the bait vector. The human Bad sequence was also PCR amplified and subdloned into the prey-vector using the same primers and subcloning strategy as described above. Human Bak was PCR amplified and subcloned as an EcoRI/XhoI fragment into vector pJG4-5 using the following primers: 5'ATC AGT GAA TTC ACT ATG GCT TCG GGG CAA GGC CC-3' (SEQ ID NO: 6) and 5' ATC GAT CTC GAG TCA GTT CAG GAT GGG ACC ATT GC-3 (SEQ ID NO: 7). Human Bax was PCR amplified and subcloned as an EcoRI/XhoI fragment into vector pJG4-5 using the following primers: 5' ATC AGT GAA TTC ACT ATG GAC GGG TCC GGG GAG-3' (SEQ ID NO: 8) and 5'-TAC AGT CTC GAG TCA GGT CAC GGT CTG CCA CGT GGG-3 (SEQ ID NO: 9). Human Bcl-2, Bcl-X-L and Bcl-X-S in the yeast 2-hybrid vector pJG4-5 were available and used as described previously by Sato et al. (*Proc. Natl. Acad. Sci.* 91:9238–9242 (1994)).

To determine if human Bad binds to any of the above Bcl-2 family members, the Bad-bait plasmid was cotransformed with every prey plasmid and the reporter plasmid p18–34 into the yeast strain EGY191. Cells were induced for 6 hours with galactose to allow expression from the prey plasmid. Expression was assayed by lysing a 100 ul aliquot of yeast cells (OD 600=0.6) in 96 well plates in Z-buffer (60 mM $Na_2HPO_4$, 40 mM $NaH_2PO4 \times H_2O$, 10 mM KCL, 1 mM $MgSO_4 \times 7$ $H_2O$) and 1 u Lyticase (Boehringer Mannhein) for 1 hour followed by addition of the substrate ONPG into a final concentration of 2 mg/ml (Sigma, St. Louis, Mo.). The reaction was stopped with 0.4 M NaOH and the plate was read at an OD 420 nm. Protein-protein interaction was measured as beta-galactosidase activity using the following equation: OD 420:(OD 600×0.1 ml×ONPG reaction time).

Results of these experiments showed that human Bad interacts with Bcl-2 and Bcl-$X_L$. However, no interactions were observed between human Bad and Bax, Bak or itself. These results are presented in FIG. 3.

EXAMPLE III

In Vitro Screening and Identification of Compounds which Modify the Binding Activity of Human Bad This Example shows the screening and identification of compounds which inhibit human Bad interacting polypeptides and human Bad associations using recombinant human Bad polypeptides.

To screen for compounds which disrupt associations between human Bad interacting polypeptides and human Bad, an ELISA-type assay is employed. This assay format is used here due to its reliability and simplicity, however, other formats and binding assays can be substituted in place of the ELISA. In particular, the yeast-2-hybrid interaction between Bad and Bcl-$X_L$ or Bcl-2 shown in Example II can also be used as a compound screening assay.

To generate fusion proteins for these screening assays, Bad and Bcl-xL were cloned into pET-15b (Novagen) and pGEX 4T1 (Pharmacia) vectors, respectively. The pET15b-bad construct was made as follows. Full length bad cDNA was amplified by PCR using cDNA BM1 as template and primers containing NdeI (5') and XhoI (3') restriction sites (5' primer: 5'-GGG AAT TCC ATA TGT TCC AGA TCC CAG AG-3' (SEQ ID NO: 10)); 3' primer: 5'-TAC AGT CTC GAG TCA CTG GGA GGG GGC GGA GCT-3' (SEQ ID NO: 11)). The PCR product was then digested with NdeI/XhoI and ligated into the NdeI and XhoI sites of pET15b. The above primer sequences were chosen such that the bad ORF sequence would be in frame with 5' vector sequence encoding a six residue Histidine tag. The final construct was termed pET-15 6H Bad.

The pGEX-bcl-$X_L$ and pGEX Bax were constructed in similar fashion using primers containing EcoRI sites on both 5' and 3' ends (Bcl-$X_L$, 5' primer: 5'-AGT ATC GAA TTC ATG TCT CAG AGC AAC CGG-3' (SEQ ID NO: 12), BcL-$X_L$ 3' primer: 5'-ATT GAT GAA TTC GTT GAA GCG TTC CTG GCC CTT-3' (SEQ ID NO: 13), Bax-5' primer: 5'-ATC AGT CTC GAG ACT ATG GAC GGG TCC GGG GAG-3' (SEQ ID NO: 14), Bax-3' primer: 5'-TAC GAT GAA TTC GGT CAC GGT CTG CCA CGT GGG-3' (SEQ ID NO: 15). PCR products were then digested with EcoRI and ligated into the EcoRI site of pGEX 4T1. The above primer sequences were chosen such that Bcl-$X_L$ and Bax ORF sequence would be in frame with 5' vector sequence encoding a glutathione-s-transferase tag.

Proteins were purified according to methods known in the art and to protocols provided by the vendor. Briefly, pET 15-6Hbad was transformed into *E. coli* strain BL21 plysS and pGE constructs into strain XL1-Blue for protein production. Bacteria were grown in the presence of 100 μg/ml carbenicillin (and 34 μg/ml chloramphenicol in the case of BL21plysS) until reaching an O.D of 1. The cultures were induced with 1 mM IPTG and grown for an additional 3 hours. Bacteria were harvested by centrifugation, and protein isolated by sonication in 50 mM Tris, pH7 with 0.1% Triton X-100 containing protease inhibitors PMSF, leupeptin (1 mg/ml) and benzamidine (1 mM). Proteins were then purified by affinity chromatography using either nickel (for 6HBad) or glutathione (for GST Bcl-$X_L$ and GST-Bax) as the affinity ligand.

To perform the screening assays, multiwell plates were coated overnight at 4° C. with 50 μl/well of the 6HBad fusion protein (4 μg/ml) in phosphate buffered saline (PBS). The plates were then washed twice with phosphate-buffered saline containing 0.02% Tween (PBST) and blocked with PBS containing 1% BSA (150 μl/well) for 2 hours at room temperature. Prior to addition of compounds to be tested, the plates were washed twice with PBST. Test compounds were added to the wells to a final concentration of about 20 μM (50 μl/well) in PBST+0.5% BSA. The plates were then incubated for 1 hour at room temperature. GST-Bcl-$x_L$ fusion protein (liquid phase) at about 1.5 μg/ml in PBST+

0.5% BSA was then added to the plates (50 µl/well) and incubated for 2 hours at room temperature. As a positive control, GST-Bcl-x$_L$ was added in the absence of the test compound. For a negative control, assays were performed on plates not coated with the 6HBad fusion protein.

An ELISA assay was then performed by first washing the plates five times with PBST and then adding an anti-GST monoclonal antibody (1:5000) in PBST+0.5% BSA to the well (50 µl/well). This antibody will detect the GST-Bcl-x$_L$ fusion protein that remains bound to the human Bad polypeptide on the plates. The antibody was allowed to incubate for hour at room temperature. Plates were washed five times with PBST and then incubated with goat-anti-mouse-alkaline phosphatase conjugated secondary antibody (1:1000) in PBST+0.5% BSA (50 µl/well). The secondary antibody is allowed to incubate for 1 hour at room temperature. The plates were washed five times with PBST and then incubated for 20 minutes with pNPP substrate (50 µl/well). Development of the plates was stopped by addition of 0.4M NaOH (50 µl/well). The plates were then read in a Molecular Devices plate reader at 405 nm. Compounds which inhibit the association of human Bad interacting polypeptides such as the GST-Bcl-x$_L$ fusion protein described above will result in a lower signal compared to the positive control.

Figure 4:
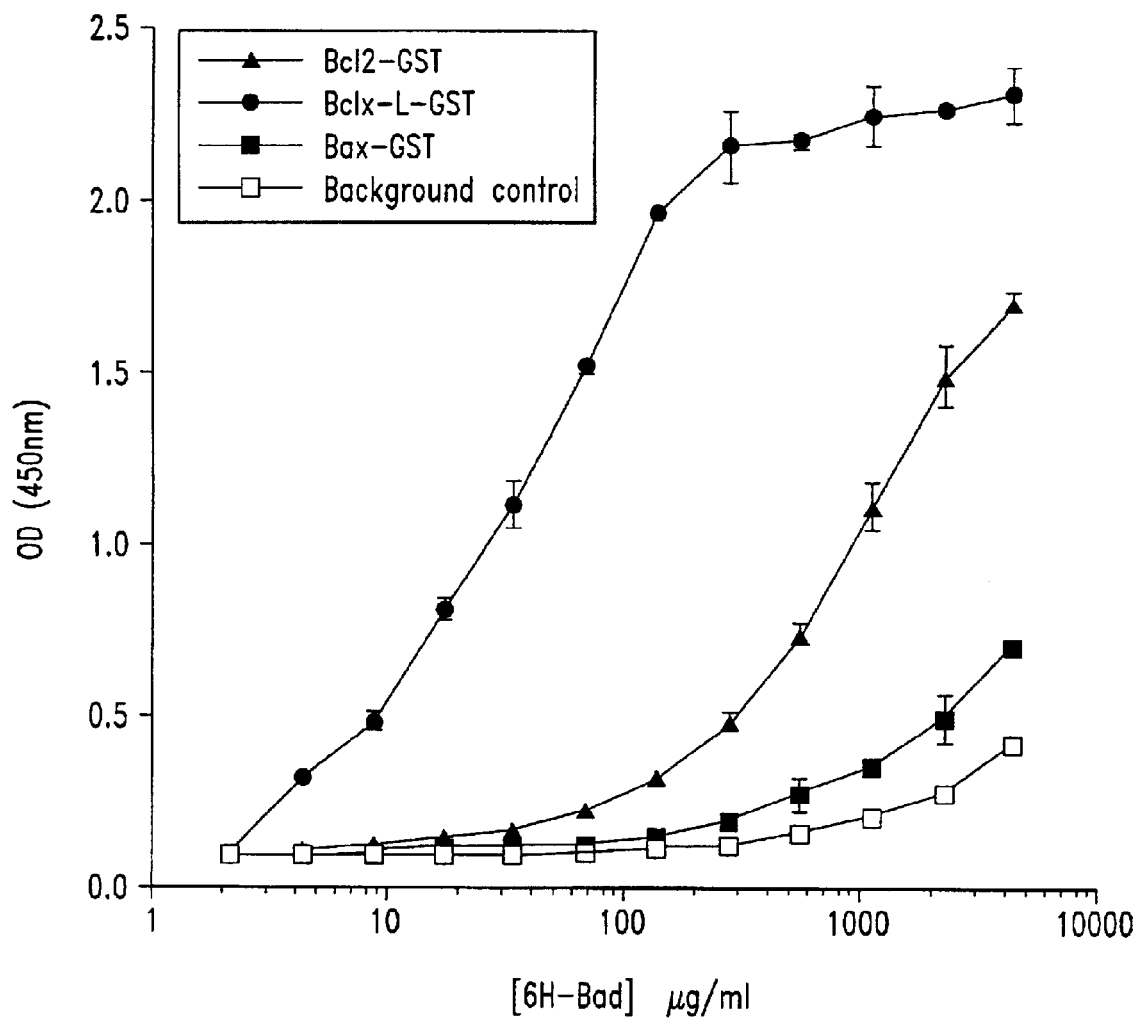
FIG. 4 shows the binding interactions between human Bad and Bcl-2 and between human Bad and Bcl-$X_L$ in an ELIZA assay.

Results of these experiments showed that human 6Had interacts with GST-Bcl-X$_L$ and GST-Bcl-2, but not with GST-Bax. 6HBad binds with highest affinity to GST-Bcl-x$_L$. These results are presented in FIG. 4.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of screening for a compound that interferes with the association of a human Bad interacting polypeptide with human Bad, said human Bad comprising an isolated human Bad polypeptide encoded by a nucleic acid molecule comprising the nucleotide sequence shown in SEQ ID NO; 1 or a nucleotide sequence that has greater than 85% nucleotide identify to the nucleotide sequence shown in SEQ ID NO:1 wherein said screening comprises contacting human Bad, or a human Bad derived fragment which retains the ability to interact with a human Bad interacting polypeptide, in the presence of an interacting polypeptide with a sample suspected of containing a compound capable of interfering with the human Bad polypeptide association and determining the interaction between human Bad and human Bad interacting polypeptide thereby screening for a compound which interferes with the association of a human Bad interacting polypeptide with human Bad.

2. The method of claim 1, wherein said interaction is a binding interaction.

3. The method of claim 1, wherein said human Bad interacting polypeptide comprises Bcl-$X_L$.

4. The method of claim 1, wherein said human Bad interacting polypeptide comprises Bcl-2.

5. The method of claim wherein said Bad fragment is a Bcl-$X_L$ binding domain.

6. The method of claim 1, wherein said Bad fragment comprises a fragment of no greater than 95 contiguous amino acids of the 3' end of SEQ ID NO:2, wherein the fragment binds Bcl-$X_L$ or Bcl-2 and wherein the fragment contains at least one amino acid that differs when aligned with SEQ ID NO:3.

7. The method of claim 2, wherein said binding is determined by the detection of a reporter gene.

8. The method of claim 2, wherein said binding is determined by an enzyme linked immunosorbant assay (ELISA).

* * * * *

UNITED STATES PATENT AND TRADEMARK OFFICE
CERTIFICATE OF CORRECTION

PATENT NO. : 6,824,991 B2
DATED : November 30, 2004
INVENTOR(S) : William A. Horne et al.

It is certified that error appears in the above-identified patent and that said Letters Patent is hereby corrected as shown below:

Column 22,
Line 66, "claim wherein" should read as -- claim 1 wherein --.

Signed and Sealed this

Twenty-third Day of August, 2005

JON W. DUDAS
*Director of the United States Patent and Trademark Office*

SEQUENCE LISTING

<160> NUMBER OF SEQ ID NOS: 15

<210> SEQ ID NO 1
<211> LENGTH: 946
<212> TYPE: DNA
<213> ORGANISM: Homo sapiens

<400> SEQUENCE: 1

```
gggcctaggg cgccgggtca ggggcctcga gatcgggctt gggcccagag catgttccag      60
atcccagagt ttgagccgag tgagcaggaa gactccagct ctgcagagag gggcctgggc     120
cccagccccg caggggacgg gccctcaggc tccggcaagc atcatcgcca ggccccaggc     180
ctcctgtggg acgccagtca ccagcaggag cagccaacca gcagcagcca tcatggaggc     240
gctggggctg tggagatccg gagtcgccac agctcctacc ccgcggggac ggaggacgac     300
gaagggatgg gggaggagcc cagcccctttt cggggccgct cgcgctcggc gcccccaac      360 ctctgggcag cacagcgcta tggccgcgag ctccggagga tgagtgacga gtttgtggac     420
tcctttaaga agggacttcc tcgcccgaag agcgcgggca cagcaacgca gatgcggcaa     480
agctccagct ggacgcgagt cttccagtcc tggtgggatc ggaacttggg caggggaagc     540 tccgcccct cccagtgacc ttcggtccac atcccgaaat ccaccccgtt ccattgccct     600
gggcagccat tttgaatatg ggaggaagta agttccctca ggcctatgca aaaagaggat     660
ccgtgctgta tcctttggag ggagggttga cccagattcc cttccggtgt gtgtgaagcc     720
acggaaggtt ggtcccatcg gaagttttgg gttttccgcc cacagccgcc ggaagtggct     780
ccgtggcccc gccctcaggt tccggggttt cccccaggcg cctgcgctaa gtagcgagcc     840
aggtttaacc gttgtgtcac cgggacccga gccccgcga tgccctgggg gccgtgatca     900
gtaccaaatg ttaataaagc ccgcgtgtgt gccaaaaaaa aaaaaa                     946
```

<210> SEQ ID NO 2
<211> LENGTH: 168
<212> TYPE: PRT
<213> ORGANISM: Homo sapiens

<400> SEQUENCE: 2

```
Met Phe Gln Ile Pro Glu Phe Glu Pro Ser Glu Gln Glu Asp Ser Ser
 1               5                  10                  15
```

-continued

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 3
<211> LENGTH: 204
<212> TYPE: PRT
<213> ORGANISM: Mus musculus

<400> SEQUENCE: 3

Met Gly Thr Pro Lys Gln Pro Ser Leu Ala Pro Ala His Ala Leu Gly
1               5                   10                  15

Leu Arg Lys Ser Asp Pro Gly Ile Arg Ser Leu Gly Ser Asp Ala Gly
            20                  25                  30

Gly Arg Trp Arg Pro Ala Ala Gln Ser Met Phe Gln Ile Pro Glu
        35                  40                  45

Phe Glu Pro Ser Glu Gln Glu Asp Ala Ser Ala Thr Asp Arg Gly Leu
    50                  55                  60

Gly Pro Ser Leu Thr Glu Asp Gln Pro Gly Pro Tyr Leu Ala Pro Gly
65                  70                  75                  80

Leu Leu Gly Ser Asn Ile His Gln Gln Gly Arg Ala Ala Thr Asn Ser
                85                  90                  95

His His Gly Gly Ala Gly Ala Met Glu Thr Arg Ser Arg His Ser Ser
            100                 105                 110

Tyr Pro Ala Gly Thr Glu Glu Asp Glu Gly Met Glu Glu Glu Leu Ser
            115                 120                 125

Pro Phe Arg Gly Arg Ser Arg Ser Ala Pro Pro Asn Leu Trp Ala Ala
            130                 135                 140

Gln Arg Tyr Gly Arg Glu Leu Arg Arg Met Thr Asp Glu Phe Glu Gly
145                 150                 155                 160

Ser Phe Lys Gly Leu Pro Arg Pro Lys Ser Ala Gly Thr Ala Thr Gln
                165                 170                 175

Met Arg Gln Ser Ala Gly Trp Thr Arg Ile Ile Gln Ser Trp Trp Asp
            180                 185                 190

Arg Asn Leu Gly Lys Gly Gly Ser Thr Pro Ser Gln
            195                 200

<210> SEQ ID NO 4

```
<211> LENGTH: 33
<212> TYPE: DNA
<213> ORGANISM: Artificial Sequence
<220> FEATURE:
<223> OTHER INFORMATION: PCR primer

<400> SEQUENCE: 4
atcagtgaat tcactatgtt ccagatccca gac                              33

<210> SEQ ID NO 5
<211> LENGTH: 33
<212> TYPE: DNA
<213> ORGANISM: Artificial Sequence
<220> FEATURE:
<223> OTHER INFORMATION: PCR primer

<400> SEQUENCE: 5
atcgatctcg agtcactggg aggggcgga gct                               33

<210> SEQ ID NO 6
<211> LENGTH: 35
<212> TYPE: DNA
<213> ORGANISM: Artificial Sequence
<220> FEATURE:
<223> OTHER INFORMATION: PCR primer

<400> SEQUENCE: 6
atcagtgaat tcactatggc ttcggggcaa ggccc                            35

<210> SEQ ID NO 7
<211> LENGTH: 35
<212> TYPE: DNA
<213> ORGANISM: Artificial Sequence
<220> FEATURE:
<223> OTHER INFORMATION: PCR primer

<400> SEQUENCE: 7
atcgatctcg agtcagttca ggatgggacc attgc                            35

<210> SEQ ID NO 8
<211> LENGTH: 33
<212> TYPE: DNA
<213> ORGANISM: Artificial Sequence
<220> FEATURE:
<223> OTHER INFORMATION: PCR primer

<400> SEQUENCE: 8
atcagtgaat tcactatgga cgggtccggg gag                              33

<210> SEQ ID NO 9
<211> LENGTH: 36
<212> TYPE: DNA
<213> ORGANISM: Artificial Sequence
<220> FEATURE:
<223> OTHER INFORMATION: PCR primer

<400> SEQUENCE: 9
tacagtctcg agtcaggtca cggtctgcca cgtggg                           36

<210> SEQ ID NO 10
<211> LENGTH: 29
<212> TYPE: DNA
<213> ORGANISM: Artificial Sequence
<220> FEATURE:
<223> OTHER INFORMATION: PCR primer

<400> SEQUENCE: 10
```

-continued

```
gggaattcca tatgttccag atcccagag                                    29

<210> SEQ ID NO 11
<211> LENGTH: 33
<212> TYPE: DNA
<213> ORGANISM: Artificial Sequence
<220> FEATURE:
<223> OTHER INFORMATION: PCR primer

<400> SEQUENCE: 11
tacagtctcg agtcactggg aggggcgga gct                                33

<210> SEQ ID NO 12
<211> LENGTH: 30
<212> TYPE: DNA
<213> ORGANISM: Artificial Sequence
<220> FEATURE:
<223> OTHER INFORMATION: PCR primer

<400> SEQUENCE: 12
agtatcgaat tcatgtctca gagcaaccgg                                   30

<210> SEQ ID NO 13
<211> LENGTH: 33
<212> TYPE: DNA
<213> ORGANISM: Artificial Sequence
<220> FEATURE:
<223> OTHER INFORMATION: PCR primer

<400> SEQUENCE: 13
attgatgaat tcgttgaagc gttcctggcc ctt                               33

<210> SEQ ID NO 14
<211> LENGTH: 33
<212> TYPE: DNA
<213> ORGANISM: Artificial Sequence
<220> FEATURE:
<223> OTHER INFORMATION: PCR primer

<400> SEQUENCE: 14
atcagtctcg agactatgga cgggtccggg gag                               33

<210> SEQ ID NO 15
<211> LENGTH: 33
<212> TYPE: DNA
<213> ORGANISM: Artificial Sequence
<220> FEATURE:
<223> OTHER INFORMATION: PCR primer

<400> SEQUENCE: 15
tacgatgaat tcggtcacgg tctgccacgt ggg                               33
```